United States Patent [19]

Reddy

[11] Patent Number: 5,206,227

[45] Date of Patent: Apr. 27, 1993

[54] COMPOSITION AND USE OF PHOSPHONIC ACID, (2-HALO-2-CYANOETHENYL)-DIALKYL ESTERS AS ANITMICROBIALS

[75] Inventor: Kalakota S. Reddy, Midland, Mich.

[73] Assignee: The Dow Chemical Company, Midland, Mich.

[21] Appl. No.: 892,836

[22] Filed: Jun. 2, 1992

[51] Int. Cl.$^5$ .............. A61K 31/66; C07F 9/40
[52] U.S. Cl. .................. 514/112; 558/167
[58] Field of Search .............. 558/167; 514/112

[56] References Cited

U.S. PATENT DOCUMENTS

| | | | |
|---|---|---|---|
| 2,920,097 | 1/1960 | Frazza | 558/167 X |
| 3,140,306 | 7/1964 | Heininger | 558/396 |
| 3,621,084 | 11/1971 | Humphrey | 558/96 |
| 3,674,897 | 7/1972 | Tada et al. | 558/96 |
| 4,172,892 | 10/1979 | Nannini et al. | 514/204 |
| 4,238,405 | 12/1980 | Felix | 558/430 |
| 4,388,314 | 6/1983 | Nannini et al. | 514/205 |
| 4,529,721 | 7/1985 | Nagata et al. | 514/191 |
| 4,724,056 | 2/1988 | Doane | 204/72 |
| 5,039,702 | 8/1991 | Brandman et al. | 514/526 |

FOREIGN PATENT DOCUMENTS 0104432 8/1983 European Pat. Off.
392070 10/1973 U.S.S.R. ............ 558/167

OTHER PUBLICATIONS

Arbusow, B. A., *Pure App. Chem.*, vol. 9, pp. 307–335, 1964, "Michaelis–Arbusow–und Perkow–Reaktionen".

*Primary Examiner*—Mary C. Lee
*Assistant Examiner*—Michael G. Ambrose

[57] ABSTRACT

Phosphonic acid, (2-halo-2-cyano ethylenyl)-dialkylesters are prepared which correspond to the formula:

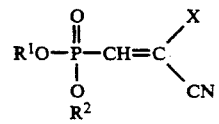

wherein $R^1$ and $R^2$ independently represent an alkyl group and X represents a halogen.

These compounds have been found to exhibit antimicrobial activity in industrial and commercial applications and compositions containing these compounds are so employed.

17 Claims, No Drawings

COMPOSITION AND USE OF PHOSPHONIC ACID, (2-HALO-2-CYANOETHENYL)-DIALKYL ESTERS AS ANITMICROBIALS

BACKGROUND OF THE INVENTION

The field of this invention is novel substituted phosphonic acid compounds and their use as antimicrobial agents.

U.S. Pat. No. 5,039,702 discloses an α-halo-β-(substituted)thio-acrylonitrile of the formula:

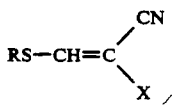

wherein X is a halogen and R is a lower alkyl, aryl, aralkyl, heterocyclo, or a thiocarbonyl group. This compound is taught to be useful as an effective antimicrobial agent.

The desirability of identifying or discovering new antimicrobial agents is widely recognized. New antimicrobial agents are desired for several reasons: these include, but are not limited to, responding to the problem created by the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves these problems by disclosing a new compound which may be employed as an antimicrobial.

SUMMARY OF THE INVENTION

The present invention is a compound corresponding to the formula:

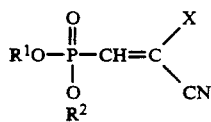

Formula 1 wherein $R^1$ and $R^2$ independently represent an alkyl group, and X represents a halogen.

The present invention is also an antimicrobial composition comprising an inert carrier and an antimicrobially effective amount of a compound of Formula 1.

The present invention is also a method for inhibiting microorganisms in a microbial habitat comprising contacting said microbial habitat with an antimicrobially effective amount of a compound of Formula 1.

DETAILED DESCRIPTION OF THE INVENTION

The present invention is a phosphonic acid, (2-halo-2-cyanoethenyl)-dialkyl ester compound corresponding to the formula:

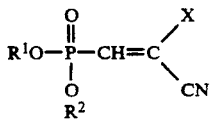

wherein $R^1$ and $R^2$ independently represent an alkyl group, and X represents a halogen.

In the present specification and claims, the term "halogen" is employed to designate fluorine, chlorine, bromine, iodine, or astatine. Preferably, halogen is employed to designate chlorine, bromine, or iodine.

In the present specification and claims, the term "alkyl" is employed to designate straight chain and branched chain alkyls. Such alkyls may be with or without substituents, such as halogen. Preferably, the term "alkyl" is employed to designate straight chain alkyls of 1 to 6 carbon atoms and branched chain alkyls of 3 to 6 carbon atoms. Most preferably, the term "alkyl" is employed to designate straight chain alkyls of 1 to 4 carbon atoms, such as methyl, ethyl, propyl or butyl and branched chain alkyls of 3 to 4 carbon atoms, such as isopropyl or tertiary butyl.

The phosphonic acid, (2-halo-2-cyanoethenyl)-dialkyl ester compounds of the present invention may be prepared, for example, by the reaction of a 2,3-dihalopropenenitrile with a trialkyl phosphite under reactive conditions. The general reaction scheme for this reaction is as follows:

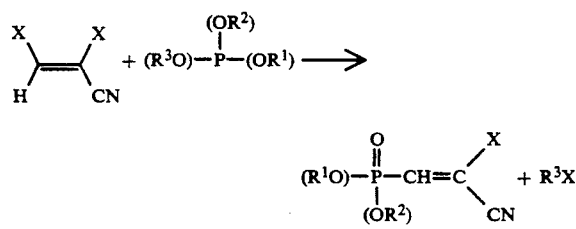

wherein $R^1$, $R^2$ and $R^3$ independently represent an alkyl group, and X represents a halogen.

In carrying out this reaction, the 2,3-dihalopropenenitrile and the trialkyl phosphite are typically contacted together in substantially equimolar amounts. The reaction is typically carried out at room temperature under an ambient pressure of an inert gas. Typically, any order of addition of the reagents may be used and the reagents may be added neat. Subsequent to the addition of the appropriate reaction reagents, the reaction mixture will typically be allowed to continue at a temperature of between about 25° C. to about 80° C. over a period of about 1 to about 24 hours. The reaction product may typically be isolated by adding a 3 to 10 volume excess of water which will precipitate the desired product. Filtration followed by washing and drying yields the desired compounds of the present invention.

Preparation of Starting Materials

The synthesis of 2,3-dichloroacrylonitrile is straightforward and is described in the art. Typically, the synthesis of 2,3-dichloroacrylonitrile begins with the chlorination of acrylonitrile to form 2,2,3-trichloropropionitrile. This chlorination is straightforward and is described in the art, such as in N. C. Lorette, "The Addition of Chlorine to Acrylonitrile", *J. Org. Chem.*, Vol. 26, pp. 2324-2327, 1960. Overall yields of over 90 percent based on acrylonitrile are achievable.

Dehydrochlorination of 2,2,3-trichloropropionitrile yields an isomeric mixture of 2,3-dichloroacrylonitrile This dehydrochlorination can be carried out by heating the 2,2,3-trichloropropionitrile in the presence of a catalyst. Purification of the 2,3-dichloroacrylonitrile prior to subsequent reaction is optional. This dehydrochlorination is straightforward and is described in the art, such as in U.S. Pat. No. 2,385,550 or U.S. Pat. No. 3,527,787.

The synthesis of trialkyl phosphites is straightforward and is described in the art, such as in U.S. Pat. No. 3,621,084: U.S. Pat. No. 3,674,897: and U.S. Pat. No. 4,724,056.

The following examples illustrate the present invention and the manner by which it can be practiced but, as such, should not be construed as limitations upon the overall scope of the same.

EXAMPLE 1

Preparation of Phosphonic Acid, (2-Chloro-2-Cyanoethenyl)-Dimethyl Ester

To 1.0 grams (g) (8.20 mmol) of 2,3-dichloro-2-propenenitrile at room temperature is added 1.02 g (8.20 mmol) of trimethyl phosphite. The reaction mixture is heated to 75° to 80° C. and stirred for 15 minutes. After 15 minutes, the reaction mixture is cooled and purified by silica gel flash column chromatography using a 1 liter ethyl acetate/hexane mixture (1:1 volume ratio) as an eluant to afford 1.25 g (78 percent yield) of product as a colorless liquid.

EXAMPLE 2

Preparation of Phosphonic Acid, (2-Choloro-2-Cyanoethenyl)-Diethyl Ester

To 1.0 g (8.20 mmol) of 2,3-dichloro-2-propenenitrile at room temperature is added 1.36 g (8.20 mmol) of triethyl phosphite. The reaction mixture is heated to 75° to 80° C. and stirred for 15 minutes. After 15 minutes, the reaction mixture is cooled and purified by silica gel flash column chromatography using a 1 liter ethyl acetate/hexane mixture (1:1 volume ratio) as an eluant to afford 1.48 g (81 percent yield) of product as a colorless liquid.

The structure identities of the compounds are confirmed by proton nuclear magnetic resonance spectroscopy, carbon nuclear magnetic resonance spectroscopy, infrared spectroscopy and gas chromatography/mass spectrometry.

Antimicrobial Activity

The phosphonic acid, (2-halo-2-cyanoethenyl)-dialkyl ester compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, the compounds disclosed herein are not necessarily active at the same concentration against different microbial species. That is, there is some microorganism-to-microorganism variation in antimicrobial potency and spectrum of antimicrobial activity.

The present invention is also directed to a method for inhibiting microorganisms which comprises contacting said microorganisms or habitat thereof with an effective amount of a compound of this invention.

The antimicrobial compounds of this invention may be added directly to aqueous formulations susceptible to microbial growth, either undiluted or dissolved in organic solvents such as glycols, alcohols, or acetone. The compounds may also be added alone or in combination with other preservatives.

As used herein, the term "microorganism" is meant to refer to bacteria, fungi, viruses, algae, subviral agents and protozoa.

As used herein, the term "antimicrobially effective amount" refers to that amount of one or a mixture of two or more of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular microorganism treated and the conditions under which such microorganism or microbial habitat is treated. Also, the exact concentration of the compound to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

TABLE I

| Compound No. | Chemical Identity |
|---|---|
| A | Phosphonic acid, (2-chloro-2-cyanoethenyl)-dimethyl ester |
| B | Phosphonic acid, (2-chloro-2-cyanoethenyl)-diethyl ester |

The minimum inhibitory concentration (MIC) for compounds of this invention, listed in Table I, is determined for 9 bacteria, using nutrient agar, and 7 yeast and fungi, using malt yeast agar. A one percent solution of a compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the compound is added (except in the controls where no compound is added) to the respective test tubes so that the final concentrations are 500, 250, 100, 50, 25, 10, 5, 2.5, 1.0 and zero parts per million of the compound in the agar, thus having a known concentration of compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per milliliter of suspension of a particular bacteria. Aliquots of 0.3 ml of each of the bacterial suspensions are used to fill the individual wells of Steer's Replicator. For each microbial suspension 0.3 ml was used to fill three wells (i.e., three wells of 0.3 ml each) so that for the nine Replicator is then used to inoculate both the neutral and alkaline pH nutrient agar petri plates.

The inoculated petri plates are incubated at 30° C. for 48 hours and then read to determine if the compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC test described above along with their respective American Type Culture Collection (ATCC) identification numbers.

TABLE II

| Organisms used in the Minimum Inhibitory Concentration Test | |
|---|---|
| Organism | ATCC No. |
| Bacteria | |
| Bacillus subtilis (BS) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables III and IV, the MIC values of the compounds as compared to the MIC of a standard commercial preservative (with 1-(3-chloroallyl)-3,5,7-triaza-1-azoniaadamantane chloride as the active agent, referred to in Tables III and IV as "STANDARD") are set forth for the bacteria organisms and yeast/fungi organisms which are listed in Table I. As can be seen from Tables III and IV, the phosphonic acid, (2-halo-2-cyanoethenyl)-dialkyl ester compounds generally achieve comparable or better antimicrobial results than the standard commercial preservative. With such antimicrobial activity, compounds of this invention should have the ability to serve as a preservative in a variety of formulated industrial, household, and commercial products such as latex, tape joint, hand lotion, and shampoo compositions.

TABLE III

| | Minimum Inhibitory Concentrations for Test Compounds in Bacteria Species (in ppm) | | | | | | | | |
|---|---|---|---|---|---|---|---|---|---|
| | ORGANISMS | | | | | | | | |
| Compound | Bs | Ea | Ec | Kp | Pv | PRD | Pa | Sc | Sa |
| STANDARD | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| Compound A | | | | | | | | | |
| pH 6.8 | 25 | 500 | 250 | 250 | 250 | 500 | 500 | 250 | 50 |
| pH 8.2 | 500 | >500 | >500 | 500 | >500 | >500 | >500 | >500 | >10 |
| Compound B | | | | | | | | | |
| pH 6.8 | 25 | 100 | 50 | 50 | 25 | 250 | 250 | 25 | 25 |
| pH 8.2 | >500 | >500 | >500 | >500 | >500 | >500 | >500 | >500 | >500 |

TABLE IV

| | Minimum Inhibitory Concentrations for Test Compounds in Yeast/Fungi Species (in ppm) | | | | | | |
|---|---|---|---|---|---|---|---|
| | ORGANISMS | | | | | | |
| COMPOUND | An | Ca | Pc | Sc | Tv | Ap | Fo |
| STANDARD | >500 | >500 | >500 | 500 | >500 | >500 | >500 |
| A | 250 | 100 | 50 | 100 | 100 | — | 50 |

TABLE IV-continued

| | Minimum Inhibitory Concentrations for Test Compounds in Yeast/Fungi Species (in ppm) | | | | | | |
|---|---|---|---|---|---|---|---|
| | ORGANISMS | | | | | | |
| COMPOUND | An | Ca | Pc | Sc | Tv | Ap | Fo |
| B | 250 | 100 | 100 | 250 | 100 | — | 50 |

What is claimed is:

1. A compound corresponding to the formula:

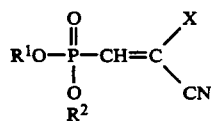

wherein $R^1$ and $R^2$ independently represent an alkyl group, and X represents a halogen.

2. The compound of claim 1 wherein $R^1$ and $R^2$ independently represent a straight chain alkyl group of 1 to 4 carbon atoms.

3. The compound of claim 2 wherein $R^1$ and $R^2$ independently represent methyl or ethyl.

4. The compound of claim 1 wherein X represents chlorine.

5. The compound of claim 1 wherein $R^1$ and $R^2$ both represent methyl or ethyl and X represents chlorine.

6. An antimicrobial composition comprising an inert carrier and an antimicrobially effective amount of a compound corresponding to the formula:

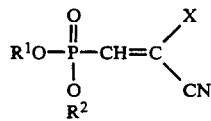

wherein $R^1$ and $R^2$ independently represent an alkyl group, and X represents a halogen.

7. The composition of claim 6 wherein the compound is present in the composition in an amount to provide from about 1 part per million to about 5,000 parts per million by weight of the compound to a microbial habitat that is contacted with the composition.

8. The composition of claim 6 wherein $R^1$ and $R^2$ independently represent a straight chain alkyl group of 1 to 4 carbon atoms.

9. The composition of claim 8 wherein $R^1$ and $R^2$ independently represent methyl or ethyl.

10. The composition of claim 6 wherein X represents chlorine.

11. The composition of claim 6 wherein $R^1$ and $R^2$ both represent methyl or ethyl and X represents chlorine.

12. A method for inhibiting microorganisms in a microbial habitat comprising contacting said microbial habitat with an antimicrobially effective amount of a compound corresponding to the formula:

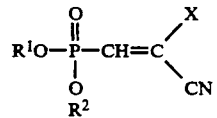

wherein $R^1$ and $R^2$ independently represent an alkyl group, and X represents a halogen.

13. The method of claim 12 wherein the compound is present in an amount to provide from about 1 part per million to about 5,000 parts per million by weight of the compound to the microbial habitat.

14. The method of claim 12 wherein $R^1$ and $R^2$ independently represent a straight chain alkyl group of 1 to 4 carbon atoms.

15. The method of claim 14 wherein $R^1$ and $R^2$ independently represent methyl or ethyl.

16. The method of claim 12 wherein X represents chlorine

17. The method of claim 12 wherein $R^1$ and $R^2$ both represent methyl or ethyl and X represents chlorine.

* * * * *